(12) United States Patent
Huang et al.

(10) Patent No.: US 6,238,865 B1
(45) Date of Patent: May 29, 2001

(54) SIMPLE AND EFFICIENT METHOD TO LABEL AND MODIFY 3'-TERMINI OF RNA USING DNA POLYMERASE AND A SYNTHETIC TEMPLATE WITH DEFINED OVERHANG NUCLEOTIDES

(75) Inventors: Zhen Huang, 3211 Avenue I, Apt. 6A, Brooklyn, NY (US) 11210; Jack W. Szostak, 308 Commonwealth Ave., Boston, MA (US) 02114

(73) Assignees: Guangtian Chen, Bronx, NY (US); Zhen Huang, Brooklyn, NY (US); Jack W. Szostak, Boston, MA (US); a part interest ( * ) Notice: Subject to any disclaimer, the term of this patent is extended or adjusted under 35 U.S.C. 154(b) by 0 days.

(21) Appl. No.: 09/173,936

(22) Filed: Oct. 16, 1998

Related U.S. Application Data
(60) Provisional application No. 60/063,757, filed on Oct. 17, 1997.

(51) Int. Cl.[7] .............................. C12Q 1/68; C12P 19/34; C07H 21/02; C07H 21/04; C12N 15/00
(52) U.S. Cl. .................... 435/6; 435/91.2; 536/23.1; 536/24.3; 935/76; 935/77; 935/78
(58) Field of Search ..................... 435/6, 91.2; 536/23.1, 536/24.3; 935/76, 77, 78

(56) References Cited

U.S. PATENT DOCUMENTS
5,266,466 * 11/1993 Tabor et al. ................. 435/91.5

OTHER PUBLICATIONS
England et al., Nature 275: 560–561 (1978).*
Linger et al., 3'–end Labeling of RNA with Recombinant Yeast Ploy(A) Polymerase, Nucleic Acids Research 21(12): 2917–2920 (1993).*
The Gibco–BRL Catalog pp. 375–377 and 383–387 (1992 Edition).*
Chirala et al., Gene 47: 297–300 (1996).*
Huang et al., Nucleic Acids Research 24(21): 4360–4361 (1996).*
LeBlond et al., Analytical Biochemistry 177: 413–418 (1989).*
Oyama et al., Analytical Biochemistry 172: 444–450 (1988).*

* cited by examiner

Primary Examiner—Ethan Whisenant
(74) Attorney, Agent, or Firm—Cohen, Pontani, Lieberman & Pavane

(57) ABSTRACT

A novel 3'-terminus modified nucleic acid and a method of making such product using a synthetic nucleotide template with a defined overhang nucleotide are disclosed. The method allows an efficient incorporation of a single modified nucleotide onto the 3'-terminus of the nucleic acid.

4 Claims, 12 Drawing Sheets

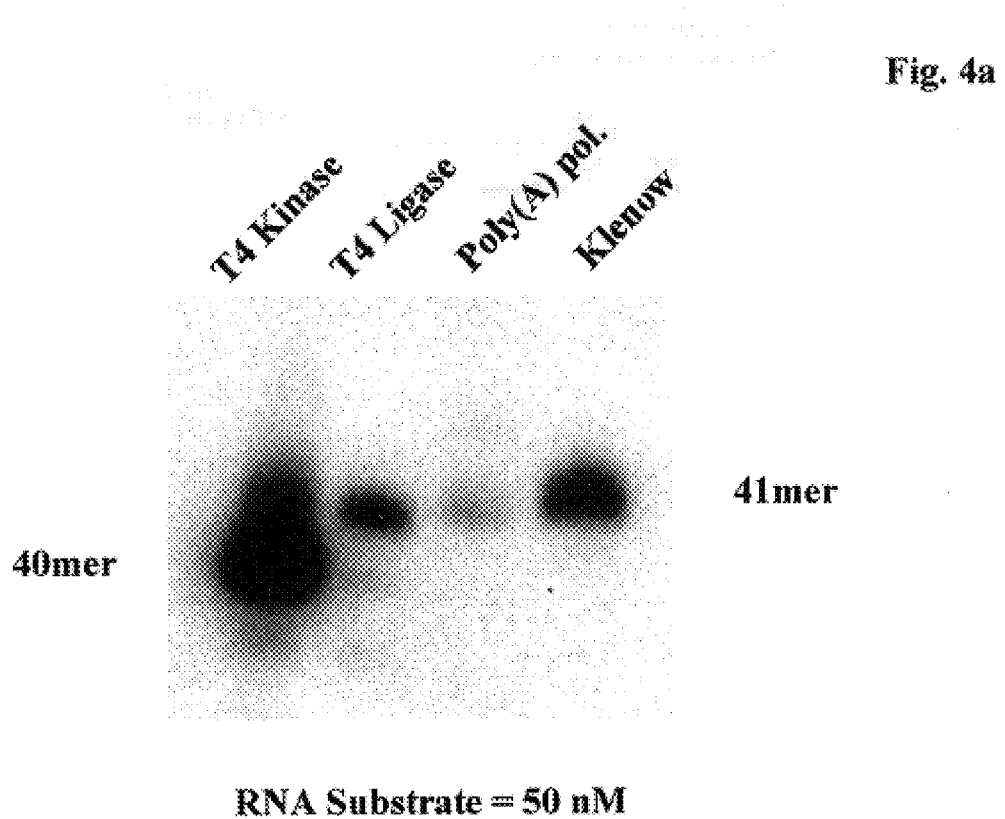

Thio-GTP Analog

SEQUENCE LISTING (1) GENERAL INFORMATION:

(iii) NUMBER OF SEQUENCES: 21

(2) INFORMATION FOR SEQ ID NO: 1:

(i) SEQUENCE CHARACTERISTICS:
      (A) LENGTH: 10 bases
      (B) TYPE: nucleic acid
      (C) STRANDEDNESS: single
      (D) TOPOLOGY: linear (ii) MOLECULE TYPE: DNA (xi) SEQUENCE DESCRIPTION: SEQ ID NO: 1:

GGGTTGCTGG                                                          10

(2) INFORMATION FOR SEQ ID NO: 2:

(i) SEQUENCE CHARACTERISTICS:
        (A) LENGTH: 11 bases
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 2:

TGGGTTGCTG G                                                        11

(2) INFORMATION FOR SEQ ID NO: 3:

(i) SEQUENCE CHARACTERISTICS:
        (A) LENGTH: 11 bases
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 3:

CGGGTTGCTG G                                                        11

(2) INFORMATION FOR SEQ ID NO: 4:

(i) SEQUENCE CHARACTERISTICS:
        (A) LENGTH: 12 bases
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 4:

TTGGGTTGCT GG                                                       12

(2) INFORMATION FOR SEQ ID NO: 5:

(i) SEQUENCE CHARACTERISTICS:
        (A) LENGTH: 13 bases
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 5:

TTTGGGTTGC TGG                                                      13

(2) INFORMATION FOR SEQ ID NO: 6:

(i) SEQUENCE CHARACTERISTICS:
        (A) LENGTH: 14 bases
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 6:

TTTTGGGTTG CTGG                                                     14

(2) INFORMATION FOR SEQ ID NO: 7:

(i) SEQUENCE CHARACTERISTICS:
        (A) LENGTH: 14 bases
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 7:

TTTTTGGGTT GCTG                                                    14

(2) INFORMATION FOR SEQ ID NO: 8:

(i) SEQUENCE CHARACTERISTICS:
        (A) LENGTH: 12 bases
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 8:

CTGGGTTGCT GG                                                        12

(2) INFORMATION FOR SEQ ID NO: 9:

(i) SEQUENCE CHARACTERISTICS:
        (A) LENGTH: 12 bases
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 9:

ATGGGTTGCT GG                                                        12

(2) INFORMATION FOR SEQ ID NO: 10:

(i) SEQUENCE CHARACTERISTICS:
        (A) LENGTH: 12 bases
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 10:

GTGGGTTGCT GG                                                        12

(2) INFORMATION FOR SEQ ID NO: 11:

(i) SEQUENCE CHARACTERISTICS:
        (A) LENGTH: 12 bases
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 11:

GTGTAGTTGA AT                                                        12

(2) INFORMATION FOR SEQ ID NO: 12:

(i) SEQUENCE CHARACTERISTICS:

(A) LENGTH: 17 bases
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 12:

GTGTAGTTGA ATCAGCA                                                          17

(2) INFORMATION FOR SEQ ID NO: 13:

(i) SEQUENCE CHARACTERISTICS:
        (A) LENGTH: 17 bases
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 13:

GTGGGTTGCT GGCACCG                                                          17

(2) INFORMATION FOR SEQ ID NO: 14:

(i) SEQUENCE CHARACTERISTICS:
        (A) LENGTH: 20 bases
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 14:

TTT TTT TTT TTT TTT TTT TT                                                  20

(2) INFORMATION FOR SEQ ID NO: 15:

(i) SEQUENCE CHARACTERISTICS:
        (A) LENGTH: 30 bases
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 15:

GGGTTGGGAA GAAACTGTGG CACTTCGGTG                                            30

(2) INFORMATION FOR SEQ ID NO: 16:

(i) SEQUENCE CHARACTERISTICS:
        (A) LENGTH: 40 bases
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 16:

GGGTTGGGAA GAAACTGTGG CACTTCGGTG CCAGCAACCC                                 40

(2) INFORMATION FOR SEQ ID NO: 17:

(i) SEQUENCE CHARACTERISTICS:
        (A) LENGTH: 19 bases
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 17:

GGGCGCCGCA CGCATCGAG                                                          19

(2) INFORMATION FOR SEQ ID NO: 18:

(i) SEQUENCE CHARACTERISTICS:
        (A) LENGTH: 38 bases
        (B) TYPE: nucleic acid
        (C) STRANDEDNESS: single
        (D) TOPOLOGY: linear (ii) MOLECULE TYPE: RNA (xi) SEQUENCE DESCRIPTION: SEQ ID NO: 18:

GGGUCGCUAA GAGACUCUGA CACCUCGAUG CGUGCGGC                                     38

(2) INFORMATION FOR SEQ ID NO: 19:

(i) SEQUENCE CHARACTERISTICS:
        (A) LENGTH: 40 bases
        (B) TYPE: nucleic acid
        (C) STRANDEDNESS: single
        (D) TOPOLOGY: linear (ii) MOLECULE TYPE: RNA (xi) SEQUENCE DESCRIPTION: SEQ ID NO: 19:

GGGUUGGGAA GAAACUGUGG CACUUCGGUG CCAGCAACCC                                   40

(2) INFORMATION FOR SEQ ID NO: 20:

(i) SEQUENCE CHARACTERISTICS:
        (A) LENGTH: 40 bases
        (B) TYPE: nucleic acid
        (C) STRANDEDNESS: single
        (D) TOPOLOGY: linear (ii) MOLECULE TYPE: RNA (xi) SEQUENCE DESCRIPTION: SEQ ID NO: 20:

GGAGAGUAUG CAGUAGUCAU CGCGACGGUG CCAGCAACCC                                   40

(2) INFORMATION FOR SEQ ID NO: 21:

(i) SEQUENCE CHARACTERISTICS:
        (A) LENGTH: 50 bases
        (B) TYPE: nucleic acid
        (C) STRANDEDNESS: single
        (D) TOPOLOGY: linear (ii) MOLECULE TYPE: RNA (xi) SEQUENCE DESCRIPTION: SEQ ID NO: 21:

GGAGAGUAUG CAGUAGUCAU CGCGACGUAG CUAGAUGCUG                                   40
AUUCAACUAC                                                                    50

SIMPLE AND EFFICIENT METHOD TO LABEL AND MODIFY 3'-TERMINI OF RNA USING DNA POLYMERASE AND A SYNTHETIC TEMPLATE WITH DEFINED OVERHANG NUCLEOTIDES

RELATED U.S. APPLICATION

This application is based on the U.S. provisional application Serial No. 60/063,757, filed on Oct. 17, 1997, which is hereby incorporated by reference in its entirety.

BACKGROUND OF THE INVENTION

1. Field of the Invention

This invention relates to 3'-terminus modified nucleic acids including DNA and RNA, and methods for modifying 3'-termini of nucleic acid compounds.

2. Description of the Related Art

Labeling RNA 3'-termini is important for studies of gene regulation at RNA level and RNA biological function in vitro or in vivo, and for clinical test and research. There are two commonly used methods for end-labeling RNA: 3'-labeling with 3',5'-[5'-$^{32}$P]-pCp and T4 RNA ligase (England, et. al., Nature, 275:560–561, 1978; Uhlenbeck, et. al., The Enzymes, Vol. XV:31–58, 1982), and 3'-labeling with [α-$^{32}$P]-cordycepin 5'-triphosphate (CoTP or 3'-deoxy-ATP) and poly(A) polymerase (Linger, et. al., Nucleic Acids Res., 21:2917–2920, 1993; Edmonds, et. al., The Enzymes, Vol. XV:217–239, 1982). The 3'-labeling methods are less satisfactory. Labeling with T4 RNA ligase requires high concentrations of pCp and enzyme, and is less efficient at labeling long RNAs (Linger, et. al., Nucleic Acids Res., 21:2917–2920, 1993). Poly(A) polymerase labels short RNAs poorly (Linger, et. al., Nucleic Acids Res., 21:2917–2920,1993) and also requires a high concentration of [α-$^{32}$P]-CoTP for optimal incorporation (Beltz, et. al., Fed. Proc., 41:1450–1455,1982).

SUMMARY OF THE INVENTION

We have developed a new method for 3'-terminus labeling or modifying nucleic acid including RNA based on the principle of synthesis of Okazaki Fragments (Okazaki, et. al., Proc. Natl. Acad. Sci. USA, 64:1242–1248, 1969). Our method allows to introduce a single nucleotide to RNA 3'-termini. It is a simple and efficient method to label or modify RNA 3'-termini using DNA polymerase and a synthetic template with defined overhang nucleotides. The ready availability of short synthetic oligodeoxynucleotides should allow any RNA of known sequence to be extended in a template-directed manner at its 3'-terminus, and therefore selectively labeled, by DNA polymerase in the presence of the appropriate dNTP (FIG. 1). After screening a number of polymerases, we found that DNA polymerase I large fragment [Klenow fragment (Gubler, et. al., Methods Enzymol., 152:330–335, 1987; Sanger, et. al., Proc. Natl. Acad. Sci. USA, 74:5463–5467, 1977)] is capable of rapidly and efficiently incorporating [α-$^{32}$P]-dATP onto RNA 3'-termini.

The various features of novelty which characterize the invention are pointed out with particularity in the claims annexed to and forming a part of the disclosure. For a better understanding of the invention, its operating advantages, and specific objects attained by its use, reference should be had to the drawing and descriptive matter in which there are illustrated and described preferred embodiments of the invention.

BRIEF DESCRIPTION OF THE DRAWINGS

In the drawings:

FIG. 4a is a comparison of RNA labeling by T4 polynucleotide kinase, T4 RNA ligase, poly(A) polymerase and DNA polymerase Klenow fragment.

DETAILED DESCRIPTION OF THE PRESENTLY PREFERRED EMBODIMENTS

Figure 1:
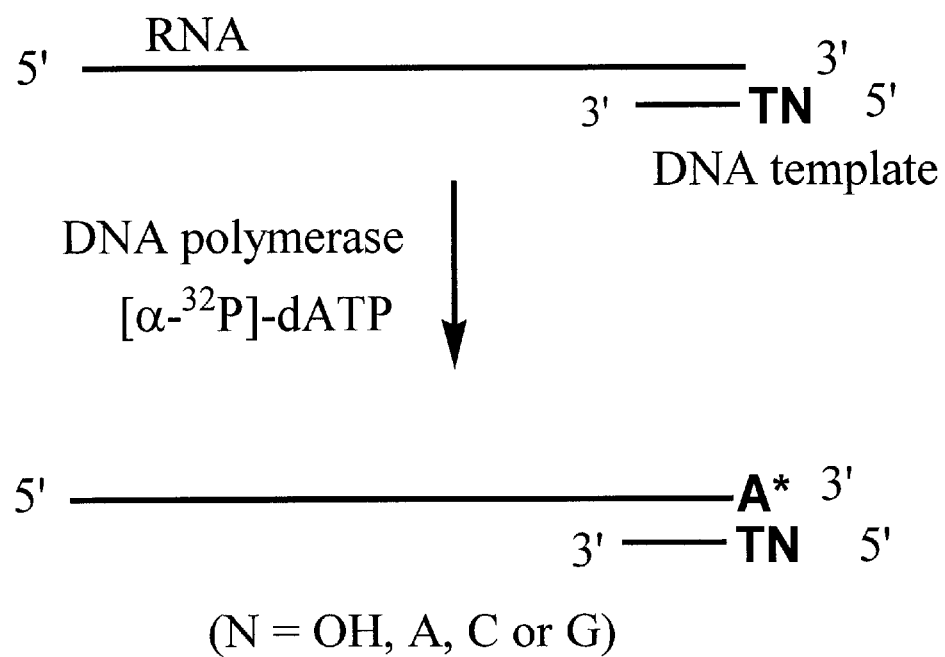
FIG. 1 is a schematic representation of 3'-terminal extension of an RNA primer on a DNA template.

We describe a simple method for 3'-end labeling RNA using the Klenow fragment of DNA polymerase I, [α-$^{32}$P]-dATP, and a short synthetic DNA template complementary to the 3'-end of the RNA. A template with an overhang of a single 5'-T allows the incorporation of one dA residue at the 3'-terminus of the RNA, but with poor efficiency. However, a template with an overhang of two nucleotides (5'-AT, 5'-CT, or 5'-GT) results in the rapid and efficient incorporation of a single dA. Low concentrations of RNA can be quickly 3'-labeled to high specific activity with this procedure. The efficiency of 3'-labeling with the Klenow fragment of DNA polymerase is comparable to that of 5'-labeling with T4 polynucleotide kinase. Since the labeling is template directed, specific RNAs within a complex mixture can be selectively labeled.

Screening Polymerases for Efficient 3'-Labeling

We screened a variety of DNA and RNA polymerases for their ability to extend the 3'-termini of RNA on a DNA template. E. coli DNA polymerase I, the Klenow fragment of E. coli DNA polymerase I, T4 DNA polymerase, T7 DNA polymerase, Taq DNA polymerase, T7 RNA polymerase, and M-MuLV reverse transcriptase, were tested by incubation with 5'-$^{32}$P-labeled RNA and a complementary DNA template with an overhang of one nucleotide, under polymerization conditions. Both Klenow and T7 DNA polymerase were capable of extending most of the RNA by one nucleotide after an 18 hr incubation in the presence of 1 mM dATP, 260 nM DNA 11.1, and 80 nM RNA 40. The other polymerases either degraded the RNA or were less efficient at extending the RNA. Under more stringent conditions (lower RNA and dATP concentration), the Klenow fragment enzyme showed a higher efficiency of RNA extension than T7 DNA polymerase. The Klenow fragment of DNA polymerase I was therefore chosen for further characterization and optimization of the 3'-labeling reaction.

General Conditions for the Labeling Reaction and Others

E. coli DNA polymerase Klenow fragment reactions were carried out for about 5 minutes to about 48 hours, preferably about 1 to 10 hours, and most preferably about 2 hours at about 16 to 45° C., preferably about 37° C., in at least 1 µl, preferably about 5 µl of a reactio mixture including a buffer comprising about 1 to 100 mM, preferably about 10 mM of Tris-HCl having a pH of about 6.5 to 8.5, preferably about 7.5, about 1 to 100 mM, preferably about 17.5 mM of DTT, and about 1 to 100 mM, preferably about 5 mM of $MgCl_2$; about 0.05 nM to 500 µM, preferably about 0.5 to 500 nM of RNA; about 0.01 µM to 10 mM, preferably about 0.1 to 100 µM of DNA template; at least 1 nM, preferably about 66 nM of [$\alpha$-$^{32}$P]-dATP (3000 Ci/mmol, 10 mCi/mL); and at least 0.01 µl, preferably about 0.5 µl of Klenow. Many other buffer conditions were also used for this reaction, the labeling efficiency varied. Generally, the reaction conditions reported here are preferred.

T4 RNA ligase reactions were carried out for 18 hr at 4° C. in 5 ml reaction mixtures containing buffer [50 mM HEPES (pH 7.5), 3.3 mM DTT, 20 mM $MgCl_2$, and 5 µM ATP], RNA 40 (50 nM), acetylated BSA (10 µg/ml), DMSO (10%), 3', 5'-[5'-$^{32}$P]-pCp [(3000 Ci/mmol, 10 mCi/ml), 660 nM], ribonuclease inhibitor (1.5 µl), and T4 RNA ligase (5 µl).

Poly(A) polymerase reactions were carried out for 1 hr at 30° C. in 5 µl reaction mixtures containing buffer [20 mM Tris-HCl (pH 7.0), 10% glycerol, 50 mM KCl, 0.7 mM $MgCl_2$, and 0.2 mM EDTA], RNA 40 (50 nM), acetylated BSA (0.1 mg/mL), [$\alpha$-$^{32}$P]-dATP [(5000 Ci/mmol, 10 mCi/mL), 400 nM], and poly(A) polymerase (60 U/µl).

T4 polynucleotide kinase reactions were carried out for 0.5 hr at 37° C. in 5 µl reaction mixtures containing buffer [70 mM Tris-HCl (pH 7.6), 10 mM $MgCl_2$, and 15 mM DTT], RNA 40 (50 nM), [$\gamma$-$^{32}$P]-ATP [(3000 Ci/mmol, 10 mCi/mL), 66 nM], and T4 polynucleotide kinase (1 U/µl).

Electrophoresis on polyacrylamide gels was used to separate oligonucleotides by size, and radioactively labeled oligonucleotides were visualized by autoradiography, as apparent to a person of ordinary skill in the art.

Optimal Template 5'-Overhangs

Figure 2A:
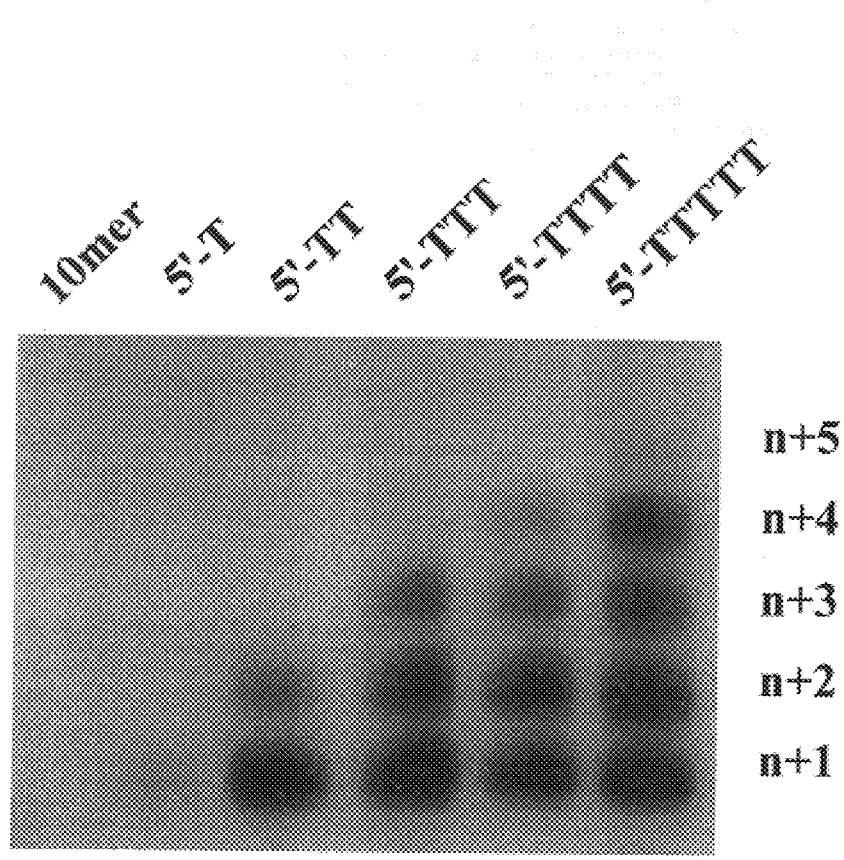
FIG. 2a shows effect of template with 5'-overhangs having a uniform nucleotide sequences on 3'-labeling of RNA with Klenow fragment and dATP.

The labeling reaction is entirely template-dependent. Templates containing 5'-OH 5'-C, 5'-G or 5'-A overhangs did not lead to RNA labeling in the presence of dATP, whereas the template with a 5'-T overhang did lead to labeling. Templates with 5'-overhangs of TT, TTT, TTTT and TTTTT were tested in order to determine the optimal length of the 5'-overhang. The oligo(T) templates led to much more efficient incorporation of dA. However the addition of increasing numbers of dA residues to the RNA resulted in a ladder of bands due to incomplete RNA extension (FIG. 2a). The degree of incorporation decreased only slightly from the bottom of the ladder to top, but the incorporation of the last nucleotide was always much less efficient than the incorporation of the preceding nucleotides.

The incorporation of [$\alpha$-$^{32}$P]-dATP onto the RNA is about 20 fold higher with a template overhang of 5'-TT than it is with 5'-T. The same efficient incorporation is obtained using templates with an overhang of 5'-CT, AT or GT (FIG. 2b), which result in the termination of the extension reaction after the addition of only a single dA residue. These templates are superior for 3'-labeling because extension of the RNA is efficient and results in a single labeled product.

Optimization of Reaction Conditions

RNA 40, SEQ ID NO: 19, (5 nM) was labeled for different incubation times at 37° C. in reaction buffer containing 10 mM Tris-HCl (pH 7.5), 17.5 mM DTT, 5 mM $MgCl_2$, DNA 12.4 template (10 µM), [$\alpha$-$^{32}$P]-dATP [(3000 Ci/mmol, 10 mCi/ml), 66 nM], and Klenow fragment (0.5 U/µl). The extent of incorporation reached half maximal in ca. 30 min. and attained its maximum level in 2 hr. The labeled product was stable and remained unchanged for several hours. After 24 hrs, some loss of label from the RNA was observed, possibly as a result of the 3'-5' exonuclease activity of the Klenow fragment enzyme. In the presence of high concentrations of DNA template, this degradation by the enzyme is largely prevented.

Figure 3A:
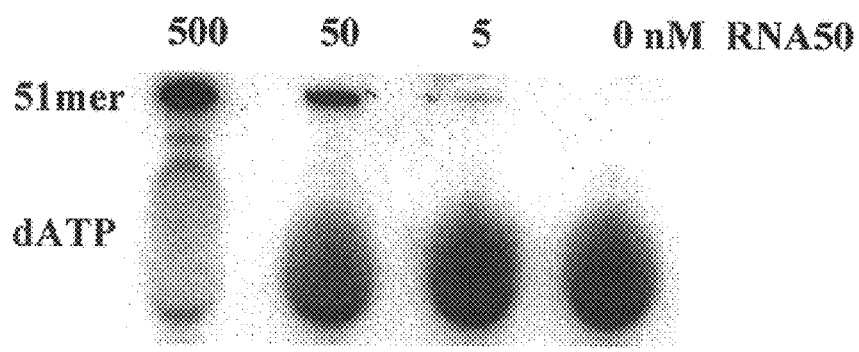
FIG. 3a shows an optimization of the concentration of RNA to be labeled.
Figure 3B:
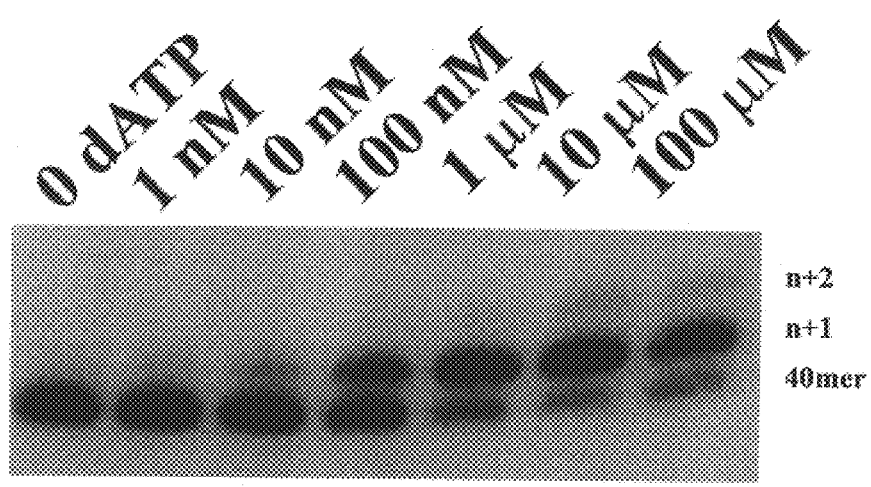
FIG. 3b shows an optimization of the concentration of unlabeled dATP.

The extent of incorporation of [$\alpha$-$^{32}$P]-dATP in a 2 hour incubation is dependent on the concentration of RNA, over the range from 0.5 nM to 500 nM. When the RNA concentration reaches 500 nM, [$\alpha$-$^{32}$P]-dATP (66 nM) incorporation is quantitative (FIG. 3a). Clearly, dATP should be present in excess over the RNA for maximal labeling efficiency. Increasing the dATP concentration from 10 to 100 µM led to more efficient conversion of the RNA (FIG. 3b). In the presence of 100 µM dATP, 100 nM RNA 40 was nearly quantitatively converted by Klenow into the single base addition product.

Figure 3C:
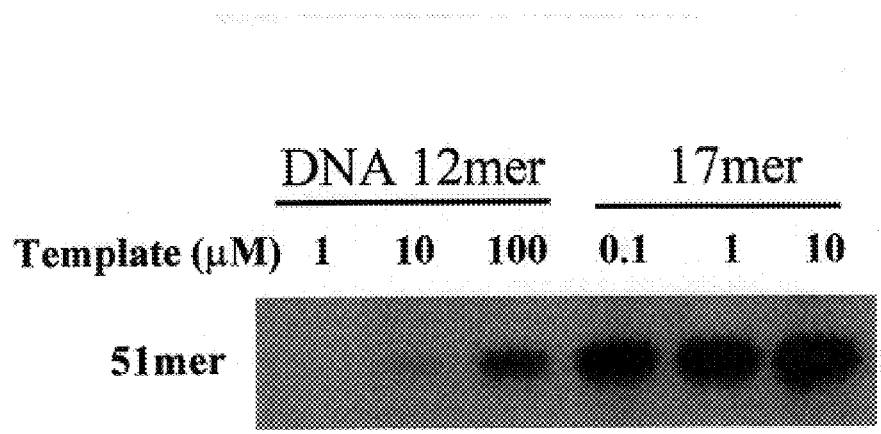
FIG. 3c shows an optimization of the concentration of templates DNA.

The effect of varying the template DNA concentration was determined for 12 and 17 nt templates with 10- and 15-nucleotide RNA/template overlaps, respectively (FIG. 3c). RNA labeling was not maximal in the presence of 100 µM of the 12-mer DNA template; in contrast, 100 nM of the 17-mer template was saturating for the extension of 50 nM RNA. Time course of the reaction was shown in FIG. 3d. In the presence of the 17-mer template (1 µM), 60% of RNA 50 (100 nM) was converted to the product with much low dATP concentration (1 µM).

Different buffers having different salt concentrations, different deoxynucleotides such as dATP, dCTP, dGTP, or TTP, nucleotides such as ATP, CTP, GTP or UTP), different templates having overhang lengths varying from 1 to 10 nt and complementary regions varying from 5 to 20 nt have been tested and the reaction efficiency varied. Other buffer systems, nucleotides or their derivatives, and templates, which are apparent to the one of ordinary skill in the art, may be also used according to the present invention.

We also observed template-directed 3'-labeling of DNA under the same conditions. The efficiency of labeling of DNA 40, SEQ ID NO: 16 using the 12-mer template was ca. 7 times less than that of RNA 40, probably because of weaker binding of the DNA template to a DNA primer as opposed to an RNA primer.

Comparison with Other Labeling Procedures

Figure 4B:
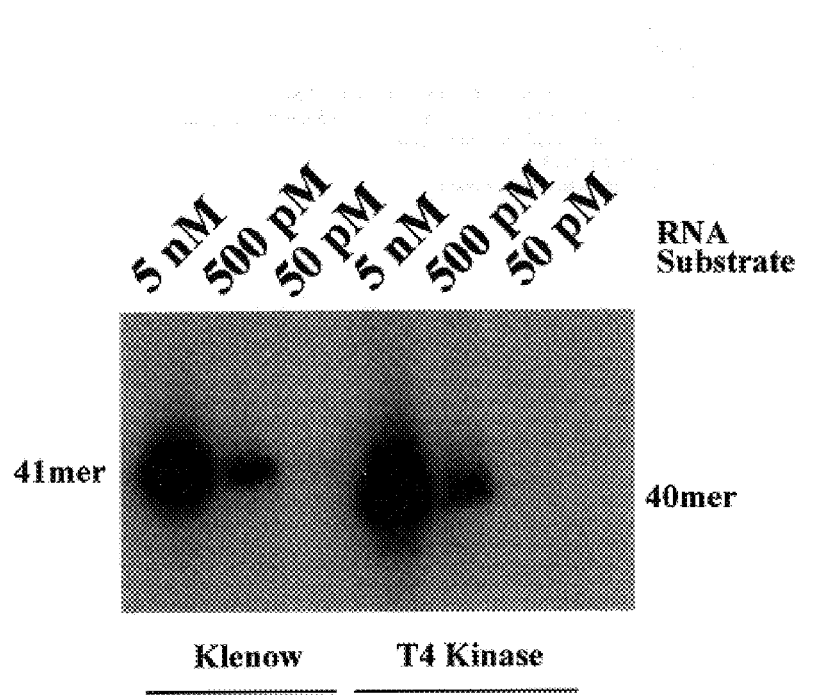
FIG. 4b is a comparison of RNA labeling by T4 polynucleotide kinase and Klenow Fragment at lower substrate concentrations.

Labeling of RNA with the Klenow fragment of DNA polymerase I was compared to labeling with T4 RNA ligase, poly(A) polymerase, and T4 polynucleotide kinase (FIG. 4a). Although the Klenow 3'-labeling is not quite as good as 5'-labeling with T4 polynucleotide kinase, at lower RNA substrate concentration, the efficiency of the Klenow labeling is comparable to that of T4 polynucleotide kinase (FIG. 4b). In contrast, poly(A) polymerase is very inefficient at labeling low concentrations (50 nM) of short RNAs such as RNA 40. T4 RNA ligase labels RNA efficiently only in the presence of a high concentration of the ligase and pCp, and was less efficient than Klenow fragment.

Selective Labeling

Figure 5:
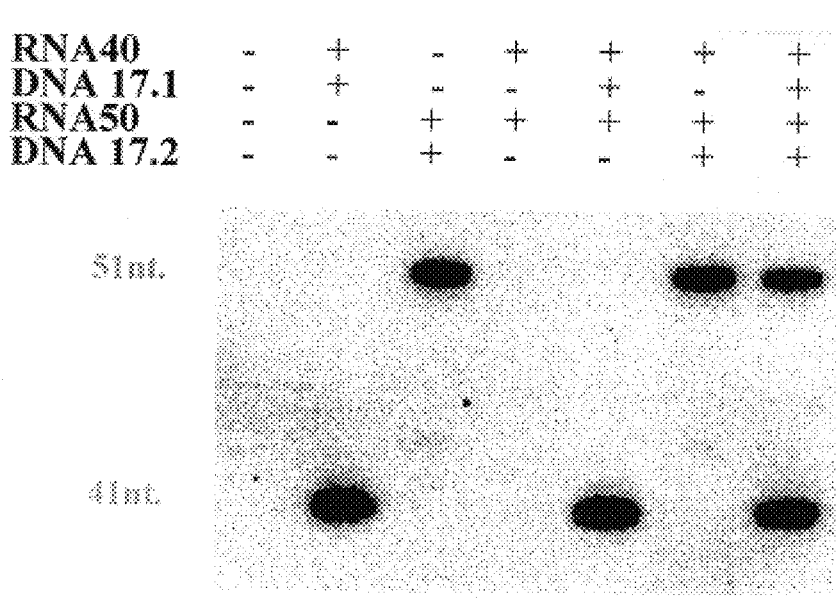
FIG. 5 shows selective 3'-labeling of one RNA in a mixture of RNAs.

Since the 3'-labeling of RNA is a template-dependent polymerization, one RNA in a mixture of RNAs can be selectively labeled. As an example, we show here that RNA 40.1, SEQ ID NO: 20, and RNA 50, SEQ ID NO: 21 can be selectively labeled by using two different templates (FIG. 5). In a mixture of RNA 40.1 and RNA 50, RNA 40.1 is specifically labeled in the presence of its complementary template, and RNA 50 is labeled when its template is added. Both RNA 40.1 and RNA 50 are labeled when both templates are added. The efficiency of labeling one oligonucleotide is not affected by the presence of the other one. This principle could also be used to label a specific DNA of known sequence in a mixture of different DNAs.

Figure 6:
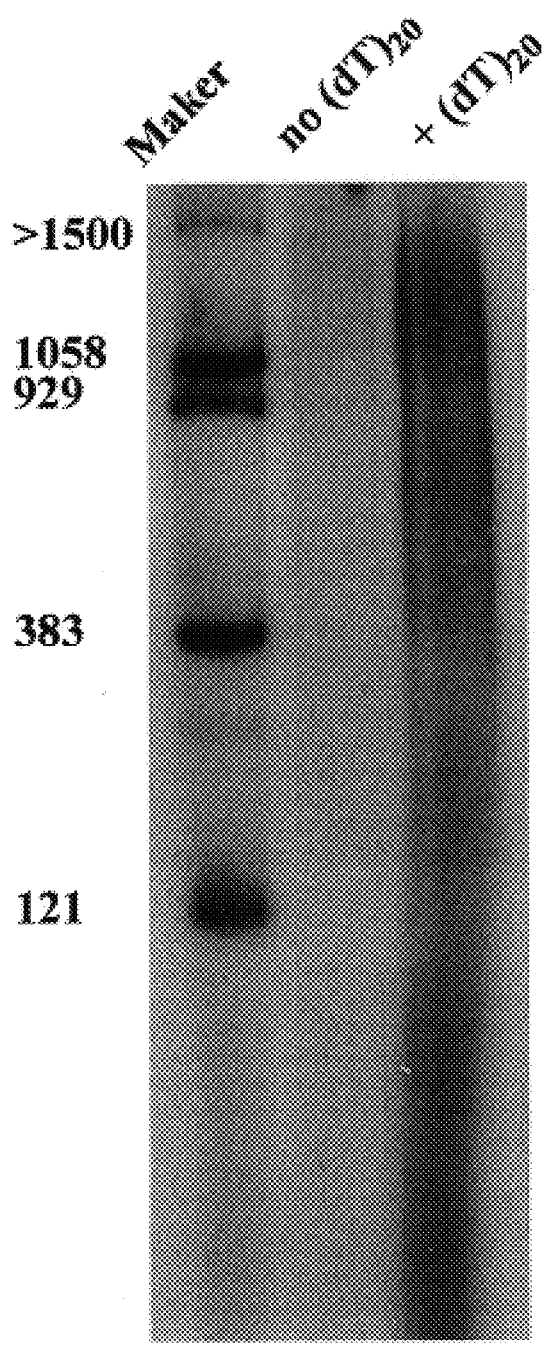
FIG. 6 shows the labeling of mRNA from human T cells with Klenow fragment and dATP.

Labeling mRNA mRNA from human leukemia T cells was successfully labeled by 3'-primer extension. mRNA is not labeled in the presence of Klenow fragment and [$\alpha$-$^{32}$P]-dATP. However, in the presence of (dT)$_{20}$, which binds to the 3'-poly(A) tail, efficient 3'-labeling of the mRNA was observed (FIG. 6).

The 3'-termini of RNA molecules can be readily labeled by using the Klenow fragment of *E. coli* DNA polymerase I to extend the 3' end of the RNA by one nucleotide on a short complementary DNA template. This method requires that the sequence of the 3'-end of the RNA be known, and that a complementary template be synthesized. However, the labeling process itself is rapid and efficient, and yields a single homogeneous labeled product. The key to increasing the efficiency of labeling to a practical level is the use of a template with a 5'-overhang of at least two nucleotides, but with a sequence (e.g. 5'-AT, 5'-CT or 5'-GT) that will cause the extension reaction to terminate after the incorporation of only one labeled nucieotide (dA in these examples).

The advantages of the method we have described stem largely from the high affinity of DNA polymerase for polynucleotides (Km=5 nM, DNA) (McClure, et. al., J. Biol. Chem., 250:4073–4080, 1975) and for dNTPs (Km=1–2 $\mu$M ) (Polesky, et. al., J. Biol. Chem., 265:14579–14591, 1990). These favorable kinetic parameters lead to the rapid labeling of low concentrations of RNA, or, if higher RNA concentrations are present, to the incorporation of a large fraction of the labeled dNTP into RNA product. In contrast, poly(A) polymerase has a lower affinity for RNA (Km=500 nM) and ATP (Km=50 $\mu$M; Km for CoTP is presumably higher) (Lingner, et. al., J. Biol. Chem., 266:8741–8746, 1991), so that labeling is rapid only at high CoTP and RNA concentrations. Also, poly(A) polymerase is more active on long than short RNA substrates. Similarly, 3'-labeling with T4 RNA ligase requires high concentrations of pCp and enzyme, and a long incubation time.

The 3'-labeling procedure described above should be useful for a variety of purposes, such as following a 3' RNA fragment in ribozyme or RNA processing reactions, labeling of 3'-termini hindered by other domains (Pyle, A. M. personal communication), and the labeling of 5'-blocked RNAs such as mRNAs (Silberklang, et. al., Eur. J. Biochem., 72:465–478, 1977; Rochat, et. al., Virus Res., 24: 137–144, 1992; Ranes-Goldberg, et. al., J. Immunol., 151:5810–5821, 1993). The ability to selectively label one RNA species in a complex mixture could also be useful (Wang, et. al., Proc. Natl. Acad. Sci. USA, 86:9717–9721, 1989); for example, T7 RNA polymerase often generates RNAs with heterogeneous 3'-termini—it should be possible to label just one of these transcripts. For some experiments it may be desirable to label an RNA with a terminal ribonucleotide, dideoxy-nucleotide or other modified nucleotide. Unfortunately, labeling with [$\alpha$-$^{32}$P]-ATP or [$\alpha$-$^{32}$P]-2',3'-ddATP was not satisfactory, probably because of the low affinity of the DNA polymerase for ribonucleotide and dideoxy-ribonucleotide triphosphates. However, recently described mutants of DNA polymerase with relaxed specificity may allow the efficient incorporation of a terminal ribonucleotide onto an RNA primer (Joyce, C. M., personal communication).

Modification of RNA 3'-Termini Using Nucleotide Triphosphate Analogs

Figure 7:
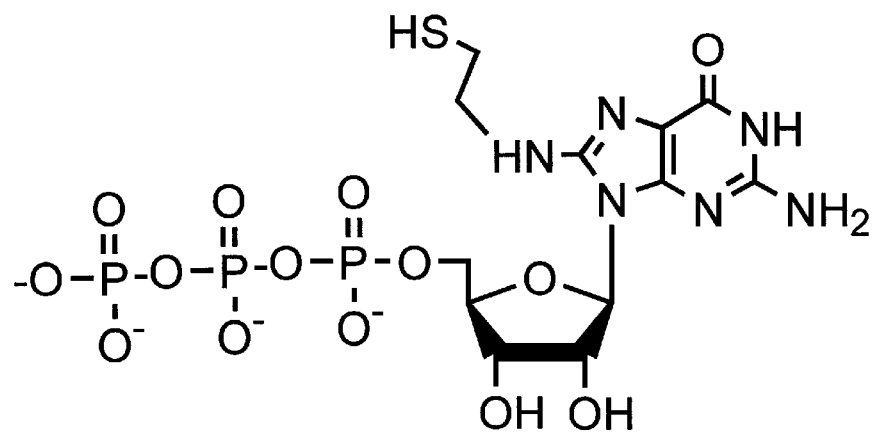
FIG. 7 is a schematic representation of incorporation of thio-GTP analog onto RNA 3'-termini on a template overhang with CGGG-5' using the terminal extension method.
Figure 7:
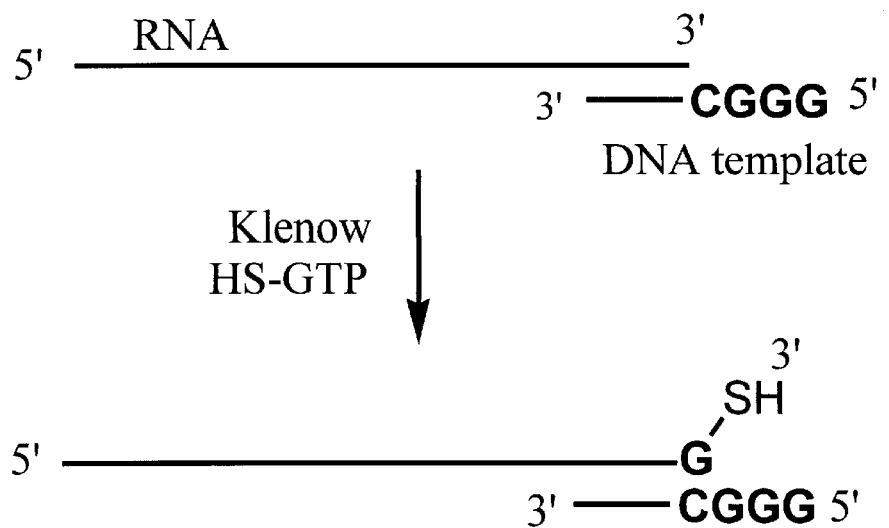
Figure 8:
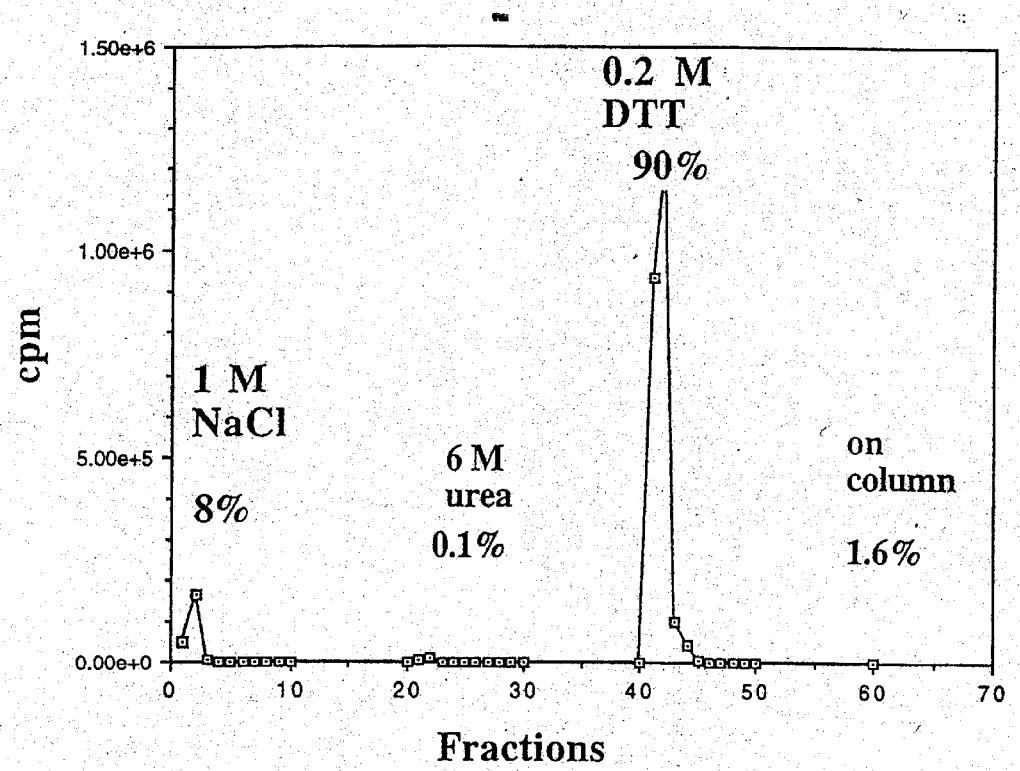
FIG. 8 shows that the thio-G containing RNA was immobilized on a thio-column via disulfide bonds while unmodified RNA was eluted by DTT solution.
Figure 9:
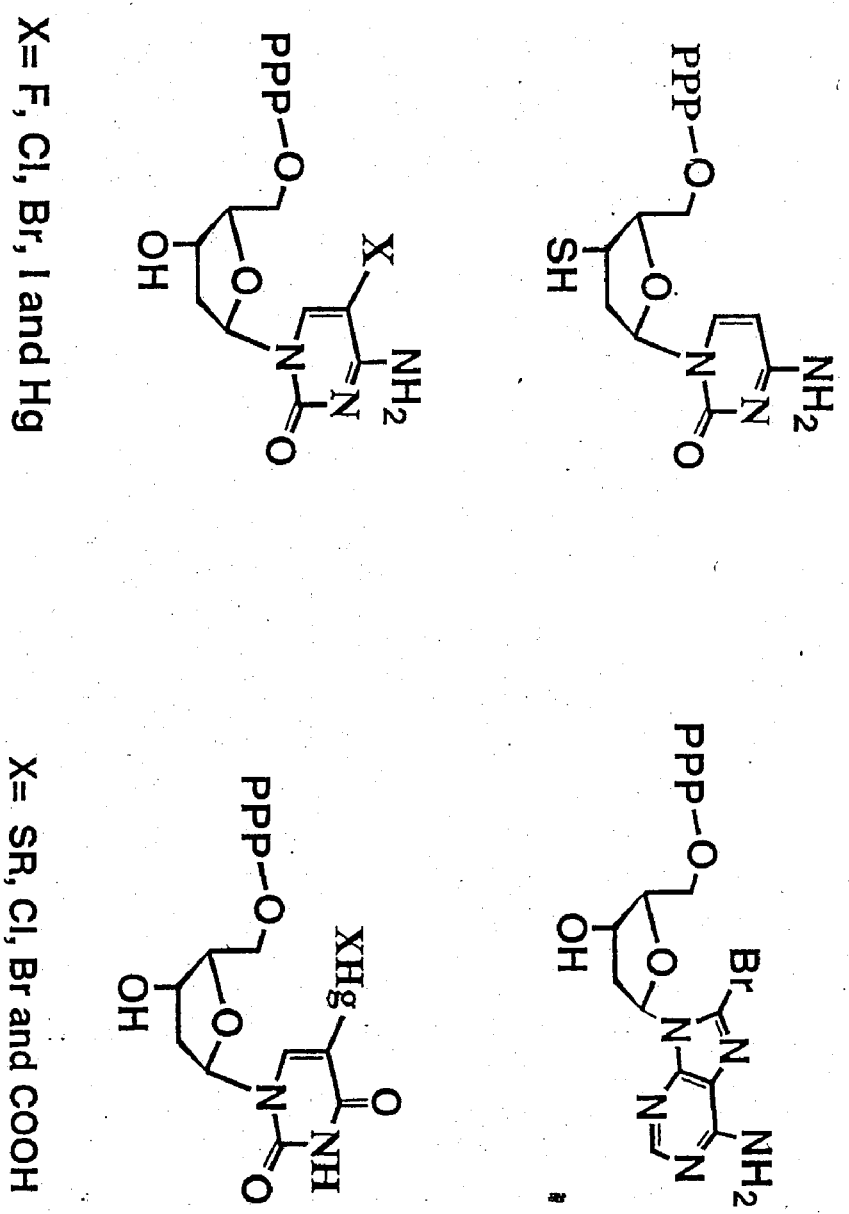
FIG. 9 shows nucleotide analogs that have been incorporated onto RNA 3'-termini using the terminal extension method.

In another embodiment, the [$\alpha$-$^{32}$P]-ATP for radioactive labeling at the 3'-terminal can be substituted by a non-radioactive nucleoside triphosphate analogs such as a thio-GTP to modify the RNA 3'-termini under the same general conditions for the labeling reaction as described above. As shown in FIGS. 7 and 8, the 3'-terminal modification reaction with the thio-GTP was carried out for 4 hr at 37° C. in 50 $\mu$l of a reaction mixture containing the reaction buffer [10 mM Tris-HCl (pH 7.5), 5 mM MgCl$_2$, 17.5 mM DTT], RNA SEQ ID NO: 18 (1 $\mu$M, 5'-GGGUCGCUAAGAGACUCUGAC-ACCUCGAUGCGUGCGGC-3'), DNA template SEQ ID NO: 17 (100 $\mu$M, 5'-GGGCGCCGCACGCA-TCGAG-3'), thio-GTP analog (1 mM) and Klenow (2 U/$\mu$l). The mononucleotide-addition reaction was satisfactory, only a trace amount of dinucleotide-addition product was observed. Many other modifications were also introduced by using different nucleoside triphosphate analogs (FIG. 8) on corresponding templates, and the reactions were satisfactory.

It is apparent to one ordinarily skilled in the art that the principle and methods described herein are applicable for the purpose of labeling or modifying 3'-termini of other nucleic acid such as DNA fragments. Conditions for such purpose can be readily determined by one skilled in the art.

EXAMPLE 1

Figure 2B:
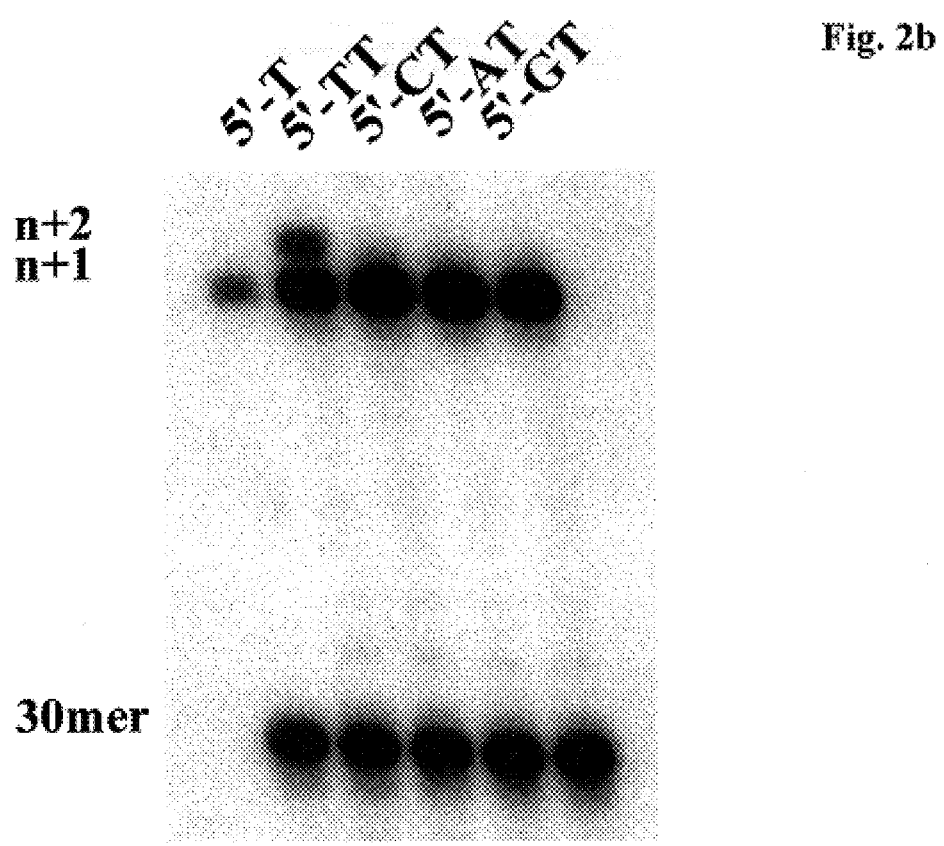
FIG. 2b shows effect of templates with 5'-overhangs having non-uniform nucleotide sequences on 3'-labeling of RNA with Klenow fragment and dATP.

Effect of Different 5'-Overhangs on 3'-Labeling of RNA with Klenow Fragment and dATP (FIG. 2a–b).

The RNA to be labeled (RNA 40$_2$), were prepared by in vitro transcription of synthetic oligodeoxynucleotide templates with T7 RNA polymerase. mRNA having a poly (A) tail was extracted from human leukemia T cells. Templates with the indicated 5'-overhangs consisting of 0 to 5 Ts, which is complementary to the modified nucleotide dATP, were DNA templates (SEQ ID NO: 1, SEQ ID NO: 2, SEQ ID NO: 4, SEQ ID NO: 5, SEQ ID NO: 6, and SEQ ID NO: 7) (100 $\mu$M in each reaction). As shown in FIG. 2a, significant additional modified nucleotides AMP are added to the 3'-terminus of the RNA when the DNA templates have overhang sequences of 5'-TTT, 5'-TTTT and 5'-TTTTT. In contrast, when using DNA templates SEQ ID NO: 8, SEQ ID NO: 9, SEQ ID NO: 10, (100 $\mu$M), the templates beginning 5'-CT, 5'-AT and 5'-GT allow efficient incorporation of a single dA residue, as shown in FIG. 2b.

Each labeling reaction mixture also contained RNA 40 (5 nM), cold dATP (2 $\mu$M), and [$\alpha$-$^{32}$P]-dATP [(3000 Ci/mmol, 10 mCi/ml), 66 nM]. A 30 mer DNA SEQ ID NO: 15 served as an internal control.

EXAMPLE 2

Optimization of Reaction Conditions (FIG. 3a–d)

As shown in FIG. 3a, the concentration of RNA to be labeled (RNA 50$^6$) was varied from 0 nM to 500 nM, and the incorporation of [α-$^{32}$P]-dATP was observed. Reaction mixtures contained template DNA 12.5, SEQ ID NO: 11 (100 μM) and [α-$^{32}$P]-dATP [(3000 Ci/mmol, 10 mCi/mL), 66 nM]. When RNA50 is 500 nM, the addition of the mononucleotide is better compared with other shown RNA50 concentrations.

FIG. 3b shows the variation of the concentration of unlabeled dATP from 0 nM to 100 mM, and the corresponding conversion of RNA to the 1-nt longer 3'-extension product. Reaction mixtures contained template DNA 12.4 (100 μM) and 5'-[$^{32}$P]-labeled RNA 40 (100 nM).

FIG. 3c shows the variation of the concentration of templates DNA 12.5 and DNAs SEQ ID NO: 12 and SEQ ID NO: 13 from 100 nM to 100 μM. Reaction mixtures contained RNA 40 (100 nM) and [α-$^{32}$P]-dATP [(3000 Ci/mmol, 10 mCi/mL), 66 nM].

Figure 3D:
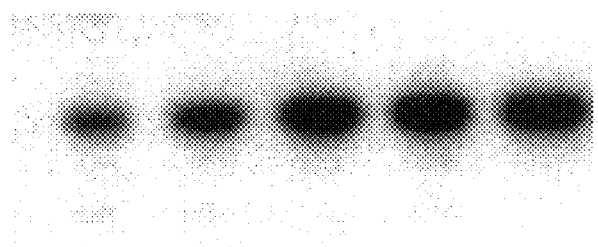
FIG. 3d shows an optimization of the reaction time.

FIG. 3d shows the determination of an optimal time of the reaction. The reaction time for producing maximum the desired products are about 2 to 4 hours.

EXAMPLE 3

Comparison of RNA labeling by T4 polynucleotide kinase T4 RNA ligase, poly(A) polymerase and Klenow Fragment (FIG. 4a–b)

As shown in FIG. 4a, the concentration of RNA 40 was 50 nM in all four labeling reactions. DNA 12.4 (100 μM) was used as a template for labeling with the Klenow fragment of DNA polymerase I. Labeling reactions were performed as described above, using [α-$^{32}$P]-dATP (3000 Ci/mmol), [γ-32P]-dATP (3000 Ci/mmol) and 3', 5'-[5'-$^{32}$P]-pCp (3000 Ci/mmol). The difference in mobility of the labeled RNAs on the gel is due to the formation of four different products in the four different labeling reactions.

FIG. 4b shows a comparison of RNA labeling by T4 polynucleotide kinase and Klenow Fragment at a RNA substrate lower concentrations between 5 nM 50 pM.

EXAMPLE 4

Selective 3'-Labeling of One RNA in A Mixture of RNAs (FIG. 5)

RNAs 40.1 and 50 were both present at 50 nM, and the DNA templates 17.1 and 17.2 were present at 1 μM. Reaction mixtures contained Klenow fragment and [α-$^{32}$P]-dATP [(3000 Ci/mmol, 10 mCi/mL), 66 nM].

EXAMPLE 5

Labeling of mRNA from Human T cells with Klenow Fragment And dATP (FIG. 6)

The labeling reaction was incubated for 2 hr at 37° C. in 5 ml of reaction buffer containing 10 mM Tris-HCl (pH 7.5), 17.5 mM DTT, and 5 mM MgCl$_2$, mRNA (17 ng/μl), template DNA 20 SEQ ID NO: 14 (100 μM), [α-$^{32}$P]-dATP [(3000 Ci/mmol, 10 mCi/ml), 660 nM], and Klenow fragment (1 U/μl).

EXAMPLE 6

Incorporation of Thio-GTP Analog into RNA (FIGS. 7–8)

The reaction conditions have been described above. The thio-G modified RNA was immobilized on a thio-column via disulfide bonds while the unmodified RNA was eluted by DTT solution (FIG. 8).

The following references are relevant to the present invention:

Beltz, W. R., et. al., Fed. Proc., 41:1450 (1982).
Edmonds, M., et. al., The Enzymes, Vol. XV, Academic Press, San Diego, pp. 217–239 (1982).
England, T. E., et. al., Nature, 275:560–561 (1978).
Gubler, U., Methods Enzymol., 152:330–335 (1987).
Linger, J., et. al., Nucleic Acids Res., 21:2917–2920 (1993).
Lingner, J., et. al., J. Biol. Chem., 266:8741–8746 (1991).
McClure, W. R., et. al., J. Biol. Chem., 250:4073–4080 (1975).
Okazaki, T., et. al., Proc. Natl. Acad. Sci. USA, 64: 1242–1248 (1969).
Polesky, A. H., et. al., J. Biol. Chem., 265:579–14591 (1990).
Rochat, R., et. al., Virus Res., 24: 137–144 (1992).
Ranes-Goldberg, M., et. al., J. Immunol., 151:5810–5821 (1993).
Sanger, F., Proc. Natl. Acad. Sci. USA, 74:5463–5467 (1977).
Silberklang, M., et. al., Eur. J. Biochem., 72:465–478 (1977).
Uhlenbeck, O. C, et. al., The Enzymes, Vol. XV, Academic Press, San Diego, pp. 31–58 (1982).
Wang, A. M., et. al., Proc. Natl. Acad. Sci. USA, 86:9717–9721 (1989).

All the references cited in this application are hereby incorporated by reference in their entirety.

The invention is not limited by the embodiments described above which are presented as examples only but can be modified in various ways within the scope of protection defined by the appended patent claims.

We claim:

1. A method for modifying a 3'-terminus of a preselected RNA sequence so as to produce a 3'-terminus modified preselected RNA sequence having at least a single modified nucleotide mono-phosphate at said 3'-terminus, comprising the steps of:

a. preparing a reaction mixture which comprises a modified nucleotide tri-phosphate selected from the group consisting of dATP, dGTP, dCTP, TTP, ATP, GTP, CTP, UTP and analogs thereof, a nucleotide template having a sequence complementary to the 3'-terminus portion of said preselected RNA sequence and a 5'-overhang sequence, said 5'-overhang sequence including at least a first overhang nucleotide mono-phosphate complementary to said modified nucleotide tri-phosphate, an enzyme capable of elongating said 3'-terminus of said preselected RNA sequence in a template dependent fashion to produce a sequence complementary to said nucleotide template, and said preselected RNA sequence to be modified at said 3'-terminus; and b. incubating said reaction mixture at 16–45° C. for at least 2 minutes to produce said 3'-terminus modified preselected RNA sequence.

2. The method of claim 1, wherein said nucleotide template has a second overhang nucleotide mono-phosphate extending from said first nucleotide mono-phosphate, said second overhang nucleotide mono-phosphate being not complementary to said modified nucleotide tri-phosphate.

3. The method of claim 2, wherein said enzyme is *E.coli* DNA polymerase Klenow fragment.

4. A kit for modifying a preselected RNA sequence so as to produce a 3'-terminus modified RNA sequence having at least a single modified nucleotide at said 3'-terminus, comprising:

a. a modified nucleotide tri-phosphate selected from the group consisting of dATP, dGTP, dCTP, TTP, ATP, GTP, CTP, UTP and analogs thereof; and b. a DNA-RNA hybrid template comprising a complementary sequence which is complementary to the 3'-terminus portion of said preselected RNA, and a 5'-overhang sequence, said 5'-overhang sequence including at least a first overhang nucleotide mono-phosphate which is complementary to said modified nucleotide tri-phosphate.

* * * * *